United States Patent [19]

Khanna et al.

[11] Patent Number: 5,212,064
[45] Date of Patent: May 18, 1993

[54] SOLID PHASE NON-SEPARATION ENZYME COMPLEMENTATION ASSAY

[75] Inventors: Pyare L. Khanna, Fremont; Imo-Jean C. Ford, Pleasant Hill; Patricia A. Porreca, Berkeley, all of Calif.

[73] Assignee: Microgenics Corporation, Concord, Calif.

[21] Appl. No.: 520,972

[22] Filed: May 9, 1990

Related U.S. Application Data

[63] Continuation of Ser. No. 261,510, Oct. 24, 1988, abandoned, which is a continuation-in-part of Ser. No. 99,396, Sep. 21, 1987, abandoned.

[51] Int. Cl.$^5$ ............... G01N 33/543; G01N 33/548; G01N 33/563
[52] U.S. Cl. ................... 435/7.6; 435/7.92; 435/7.93; 435/18; 436/512; 436/518; 436/530
[58] Field of Search ............... 435/7.6, , 7.92, 7.93, 435/18, 975; 436/512, 518, 530, 531, 533, 534, 822

[56] References Cited

U.S. PATENT DOCUMENTS

| | | | |
|---|---|---|---|
| 3,654,090 | 4/1972 | Schuurs et al. | 435/28 |
| 4,378,428 | 3/1983 | Farina et al. | 436/544 X |
| 4,708,929 | 11/1987 | Henderson | 436/501 X |
| 4,745,055 | 5/1988 | Schenk et al. | 935/11 X |

FOREIGN PATENT DOCUMENTS

WO84/03103 8/1984 PCT Int'l Appl.
WO86/02666 5/1986 PCT Int'l Appl.

OTHER PUBLICATIONS

Langley, et al., *Biochemistry* (1976) 15:4866–4875.
Langley, et al., *Proc. Natl. Acad. Sci. USA* (1975) 72:1254–1257.
Fowler, et al., *Journal of Biological Chemistry* (1978) 253(15):5521–5555.
Welpy, et al., *Journal of Biological Chemistry* (1981) 256(13):6804–6810.
Germino, et al., *Cell* (1983) 32:131–140.

Primary Examiner—David Saunders
Attorney, Agent, or Firm—Cooley Godward Castro Huddleson & Tatum

[57] ABSTRACT

Novel assays employing enzyme fragments which complex to form an active enzyme are provided. The reagents involved are a member of a specific binding pair bound to a solid surface, a first enzyme fragment conjugated to a member of a specific binding pair complementary or cross-reactive in relation to the analyte or antianalyte and a second enzyme fragment which binds to the conjugate to form an active enzyme, where the first enzyme fragment conjugate may be present in up to substantial excess to ensure at least substantially complete binding of all of the analyte. By distributing the conjugate between the solid surface and the medium in relation to the amount of analyte present, the enzyme activity may be determined in relation to the amount of analyte present, without separating the solid surface and the medium.

20 Claims, No Drawings

SOLID PHASE NON-SEPARATION ENZYME COMPLEMENTATION ASSAY

This application is a continuation of U.S. application Ser. No. 261,510, filed Oct. 24, 1988, now abandoned which is a continuation-in-part of U.S. application Ser. No. 099,396, filed Sep. 21, 1987 now abandoned.

INTRODUCTION

1. Technical Field

The measurement of analytes employing a homogeneous system involving an enzyme-donor/enzyme-acceptor and a solid surface.

2. Background of the Invention

There is a continually expanding interest in determining a wide variety of analytes in medicine, chemical processing, pollutants, and the like. Different systems are being devised which are directed to particular markets. The needs of the various markets vary, depending upon the number of assays which will be performed, the nature of the assays, the availability of skilled help, the sensitivity required, as well as other individual factors. Systems vary from being generally applicable to a wide variety of instruments, such as spectrophotometers and fluorometers, to being dedicated to a particular instrument, such as the TDx. Assays may involve the use of a solution, chromatographic column or a bibulous strip, where a number of steps may be required involving washings and separations or a system may involve merely adding the sample and then reading the result, visually or instrumentally. Various assays range in their sensitivity, response to other components, such as lipids, present in the sample, and degree of sophistication involved in obtaining a result. There is, a continuing interest in developing new assays which expands the repertoire of protocols and reagents available for the public to choose in performing assays.

3. Relevant Literature

U.S. Patent No. 4,378,428 describes the use of enzyme fragments in assay. Langley and Zabin, *Biochemistry* (1976) 15:4866–4875 and Langley et al., *Proc. Natl. Acad. Sci. USA* (1975) 72:1254–1257 describe the complementation between β-galactosidase fragments. W086/02666 and priority applications thereof describe the use of 8-galactosidase fragments in assay.

SUMMARY OF THE INVENTION

Methods and compositions are provided for determining analytes, where an enzyme donor is conjugated to a member of a specific binding pair, where the complementary member is bound to a solid support. The analyte is combined with the reagents and consecutively or subsequently enzyme acceptor added. The enzyme activity of the medium may then be related to the amount of analyte in the sample. Kits are provided for performing the assay.

DESCRIPTION OF THE SPECIFIC EMBODIMENTS

Methods and compositions are provided for detecting analytes employing a protocol which does not require separation steps. The method involves a specific binding pair where one of the members of the specific binding pair is bound to a solid substrate. A detectable signal is provided by a signal-producing system which comprises two segments of an enzyme, a smaller segment is referred to as the enzyme donor ("ED") and has fewer than about 100 amino acids. The enzyme donor acts as a label bound to a specific binding pair member. The other segment is an enzyme acceptor molecule, which complexes with the enzyme donor to form an active enzyme complex. The enzyme acceptor is substantially larger than the enzyme donor.

For the purposes of this invention, the signal-producing system will be exemplified by β-galactosidase where the enzyme donor is the N-terminal fragment included within the first 75 amino acids of β-galactosidase, usually involving a sequence of at least about 35 amino acids, which may be analogized to the CNBr2 fragment. The enzyme donor may have an identical sequence with the naturally-occurring β-galactosidase or may be modified by one or more mutations. The mutations may be as a result of convenience in preparing the enzyme donor, for example, by recombinant techniques involving restriction sites, to introduce a convenient linking group, such as a cysteine or lysine, to provide a fused protein, where the fusion may occur at the N- or C-terminus, where the fused peptide is competitive with the analyte, e.g., has an epitope which is immunologically competitive with an epitope of the analyte, or the like. The enzyme acceptor will generally be the C-terminal portion of the enzyme, generally being at least about 100 amino acids and will form with the enzyme donor an active enzyme complex. For details concerning the enzyme donor and enzyme acceptor, see U.S. application Ser. No. 721,267, filed Apr. 8, 1985, now U.S. Pat. No. 4,708,929.

The specific binding pair member/ED conjugate may be prepared by any conventional means. The specific binding pair or "mip" ("mip" is an acronym for member of an immunological pair) will be a ligand and its complementary receptor, usually an immunoglobulin. However, in some instances other than immunoglobulins will be employed as a member of the specific binding pair, and to that extent, mip is intended to include not only immunoglobulins, but other molecules which are capable of specifically binding to a spatial conformation and hydrophobic/hydrophilic distribution. Various techniques exist for introducing active sites on the mip, where such sites do not naturally exist, such as the introduction of active olefins, a sulfhydryl group active esters, azo groups, etc. The particular manner of linking is not critical to this invention and conventional linking groups may be employed. Usually, the mip/ED conjugate will either be joined by a bond directly, or by a linking group of not more than about 20 atoms in the chain, usually not more than about 10 atoms in the chain, counting the longest path in the case of cyclic compounds. Linking functionalities may include thioethers, amides, azo, etc. The ratio of mip to ED will usually be about 0.2-1: 1-0.2, more usually about 0.3-1:-1-0.3, and preferably from about 0.3-1:1 on the average. Desirably, all of the mip and ED will be present as conjugate.

The ligands may be either haptens or antigens, while the receptors will for the most part be binding proteins, such as immunoglobulins, fragments, particularly monovalent fragments, of immunoglobulins, e.g. Fab, Fv, etc., enzymes, naturally-occurring receptors, e.g., T-cell receptors, hormone receptors, surface membrane receptors, lectins, etc. For a disclosure of specific ligands and receptors, see U.S. Pat. No. 3,996,345, columns 10-17, which disclosure is incorporated herein by reference. Other analytes of interest include human retrovirus antigens, e.g. HIV—1, and -2, antibodies to such antigens, HTLV-1, and -2, cytokinins, etc.

One of the members of the specific binding pair will be bound to a macromolecule, usually a solid surface. The macromolecule will usually be greater than about 250 kda, more usually greater than about 500 kDa molecular weight. For the most part the macromolecules will be water soluble, such as polysaccharides, e.g. dextran. The solid surface may take many forms, including walls, particles, strips, membranes, or the like. A variety of solids may be used as the immobilizing support. Solids include Sepharose, Sephadex, agarose, polystyrene, polyacrylate, controlled pore glass, etc. of particular interest are particles which are substantially transparent under the conditions of the assay, such as latex particles. The containers in which the assays are carried out may be microtiter plate wells, test tubes, microfuge tubes, etc.

Either the receptor or the ligand may be immobilized to the solid support or bound to the macromolecule. For binding any convenient method of conjugation may be used. For immobilization, the receptor or ligand may be immobilized directly, by covalent conjugation to the surface, usually through a linking group, or indirectly by a receptor which binds to the ligand or receptor without interfering with the availability of at least one epitope or binding site, respectively. For example, avidin may be covalently conjugated to the surface, and the ligand or receptor covalently conjugated to biotin, so that the biotinavidin complex acts as a linkage between the mip and the surface.

The mip may be immobilized to various portions of the vessel or container of the assay, may be immobilized to particles, particularly dispersible particles, such as latex particles, polysaccharide particles, or other particles which will not interfere with the reading of the result, or other solid surface which serves to reduce the activity of the ED conjugate to provide an active enzyme. Many particles, such as latex particles, appear transparent in the assay medium, so that the assay may be considered to be homogeneous. In fact, in diagnostic methodology, homogeneous assays normally refer to a method which does not involve a separation step between bound and unbound label. In the subject assays, the assays may be considered to be homogeneous both as to the medium and as to the method.

Methods for conjugating a variety of compounds to a solid surface find extensive exemplification in the literature. See, for example, U.S. Pat. Nos. 4,366,241 and 4,533,629. The amount of complementary mip which will be present immobilized on a surface will be sufficient to ensure that all the mip/ED conjugate present in the assay medium is substantially bound to the surface, so as to minimize the background value. In this manner, a relatively low reproducible value should be obtained in the absence of any analyte. In the presence of analyte, the observed value will increase.

Different protocols may be employed for determining the analyte. Depending upon the protocol, various other reagents may be used in substantial excess of the maximum amount of analyte in the range of interest. One protocol involves binding of the mip to the solid surface, where the mip bound to the solid surface is in limited amount, normally not greater than about five times the highest amount of analyte in the analyte range of interest. The sample and immobilized mip are incubated for a reasonable time, usually at least about one minute and usually not more than about 12 hours, more usually not more than about 6 hours, and preferably not more than about 30 minutes. The enzyme donor-mip conjugate is then added, where the mip is the reciprocal member or complementary member of the immobilized mip. If desired, the sample and enzyme donor conjugate may be added simultaneously to allow for competition, rather than successively. After sufficient time for formation of complexes between the complementary mips, so that the enzyme donor conjugate may bind to available sites of the immobilized mip, the enzyme acceptor and substrate may be added and the enzyme activity of the medium determined, either in an equilibrium state, or as a rate of change of enzyme activity where the amount of immobilized enzyme donor is changing with time.

The concentration of conjugate may vary widely, depending upon the binding affinity of the complementary mips, the concentration range of interest, the time for the assay, and the like. Usually, the conjugate will not be less than about 0.5 of the lowest concentration in the range of interest of the analyte, preferably not less than about one times the lowest concentration of the analyte in the range of interest and, as indicated, may be in substantial excess, as much as tenfold excess or greater, depending upon the particular protocol. In any protocol, the particular concentrations may be optimized empirically. Various techniques for optimizing reagent concentrations may be found in the literature, e.g., *Principles of Competitive Protein Binding Assays*, William Odell ed. (1983) John Wiley and Sons, Inc., New York, N.Y., particularly at pages 141–147, and Eruk et al.; *Ann. Clin. Biochem.* (1984) 21:434–443.

An alternative protocol would involve combining the sample and the complementary mip-enzyme donor conjugate in substantial excess, so that substantially all of the analyte will bind. After sufficient time for substantially complete complex formation between complementary mips, the medium is combined with the immobilized mip which is complementary to the mip of the mip/enzyme donor conjugate. In this situation, it may be desirable to employ a monovalent receptor, such as a Fab fragment. After sufficient time for available enzyme donor conjugate to bind to the immobilized mip, where there is substantial excess of immobilized mip, the enzyme acceptor and substrate are added and the enzyme activity of the medium determined as described previously.

As before, the mip/ED conjugate may involve a ligand or receptor mip. When the analyte is a receptor, the mip of the mip/ED conjugate will be a ligand. Alternatively, where the analyte is a ligand (antibodies may also serve as ligands) then a receptor normally will be used. Various receptors will be employed, which receptors will be monovalent. That is, the receptors will have only one specific binding site. Conveniently, Fab fragments may be employed for binding. Alternatively, naturally occurring receptors may be employed, such as enzymes, serum proteins, and the like.

The mip/ED conjugate will be added in substantial excess of the highest concentration of the analyte to be measured. Therefore, there will be sufficient mip/ED conjugate to substantially saturate the analyte. Usually, the ratio of mip/ED conjugate to the highest value of the range of interest of analyte will be at least about 1.5:1 more usually about 2:1, and may be as high as 20:1 or greater. While the amount of mip/ED conjugate is not critical at the higher level, the greater the excess, the more that must be bound to the immobilized complementary mip and the greater the background value which will be observed. Thus, one selects the level of excess to minimize the incubation period and provide for sufficient reaction with analyte to obtain an accurate result over the range of interest, while limiting the amount of excess, so as to minimize the background value.

Since the analyte and the mip/ED conjugate will both be in solution, with the mip/ED conjugate being in large excess, even at relatively low concentrations of analyte, relatively short incubation times may be employed. Thus, the incubation time will usually be about at least 1 minute and not more than about 30 minutes, preferably not more than about 15 minutes and in many situations 5 minutes will suffice. The temperature of the incubation may be varied widely, depending upon the nature of the analyte, usually not less than 4° C., preferably not less than about 15° C., and not more than about 40° C., generally ranging from about 25°–37° C. While it is not necessary to incubate the analyte and mip/ED conjugate prior to the addition of the other reagents, usually it will be desirable to carry out the assay sequentially, to ensure complementary mip complex formation, rather than have a competition between the immobilized mip on the surface and analyte for the mip/ED conjugate.

Once the reaction between the analyte and the mip/ED conjugate has occurred, the assay medium may be contacted with the immobilized mip, which is complementary to the mip/ED conjugate. Thus, mip/ED conjugate which is bound to the immobilized mip will have a substantially lower capability for forming active enzyme with the enzyme acceptor (EA). Combining with the immobilized mip may mean transferring the assay medium to a different container, adding particles to the assay medium, usually with agitation, passing the assay medium through a column, or the like. The amount of immobilized complementary mip will be sufficient to bind substantially all of the mip/ED conjugate which has not complexed with analyte. Thus, the assay medium in which the measurement is made, should be substantially free, if not free, of uncomplexed mip/ED conjugate.

Large excesses of immobilized mip may be used as compared to the amount of mip/ED conjugate which is present. Usually, the excess will be at least about 10 times, more usually at least about 50 times, conveniently 100 times or more, and may be as high as 1,000 times or more. Since the immobilized mip requires the mip/ED conjugate to diffuse to the 35, surface, the amount of excess will vary depending upon the manner in which the mip has been immobilized and its availability to the mip/ED conjugate in solution.

While not essential, it will be desirable to incubate the assay medium with the immobilized mip for sufficient time to allow for uncomplexed mip/ED conjugate to bind to the immobilized mip. Usually this will require about 1 minute, more usually at least about 2 minutes and not more than about 30 minutes, usually not more than about 15 minutes, and preferably about 5 minutes.

After the incubation period, the remaining reagents are added. The remaining reagents will ususally be only the enzyme acceptor and substrate. The additional reagents may be added and readings taken over a predetermined time period, usually within about 5 seconds, more usually within about 10 seconds, preferably within about 20 seconds and readings then taken over from 10–60 second intervals for the determination. The amount of EA which is added will be sufficient to complex substantially all of the mip/ED conjugate which is not immobilized, generally being at least about equivalent to the highest concentration level of interest of the analyte, usually in excess of that amount, usually not more than about 1,000 times in excess, more usually not more than about 500 times in excess, generally at least about 2 times in excess. Once the EA and substrate has been added, the assay is carried out as a conventional ED/EA beta-galactosidase assay.

When particles are used, desirably relatively small particles will be used, generally ranging from about 20–200 nm, preferably from about 50 to 100 nm.

Since the enzyme activity at the solid surface will be substantially lower than the enzyme activity in solution, the rate observed will vary with the amount of analyte in the medium.

By using standards having known amounts of analyte, enzyme activities may be determined for a particular protocol. In this way, a standard curve may be devised under a particular set of conditions, where the results obtained with an unknown sample may be related to the standard curve to provide for a quantitative determination of analyte.

Various substrates may be employed for spectrophotometric or fluorimetric determinations. O-nitrophenyl-$\beta$-galactoside, $\beta$-galactosidyl umbelliferone, di-$\beta$-galactosidyl fluorescein, resorufin-$\beta$-galactoside may be employed. The concentration of the substrate will be in substantial excess so as not to be rate limiting.

Kits can be provided for convenient combinations of the reagents. The kits will provide the immobilized mip, the enzyme donor-mip conjugate, the enzyme acceptor and, conveniently, substrate. The various components may be supplied as lyophilized powders, dispersions, as containers, e.g., microtiter plates, or the like. The amounts of reagents can be provided, so as to be in relative proportions for the particular protocols. Other additives may be present, such as stabilizers, buffers, bacteriocides, excipients, etc. Except for fillers, the additives will generally be in relatively small amounts, usually in less than about 2 to 8%.

The following examples are offered by way of illustration and not by way of limitation.

Experimental

EXAMPLE 1

To demonstrate a solid phase homogeneous assay, an assay for digoxin was developed employing anti-digoxin Sepharose.

The general procedure is to dialyze the antidigoxin overnight at 4 C and 2 L of coupling buffer (0.1M sodium bicarbonate, pH 8.3, 0.5M NaCl), changing the buffer the following morning and continuing dialysis for at least 30 min. The protein concentration is then measured at $OD_{280nM}$ and coupling buffer is added to provide the desired concentration. Sepharose (1 g dry Sepharose equals approximately 3.5 ml hydrated Sepharose) is weighed and added to a sintered glass funnel, followed- by washing with cold 1 mM HCl at 200 ml HCl/g of Sepharose. Washing is continued for 15 min with successive additions of the HCl solution. The Sepharose is then rinsed in coupling buffer and transferred to the anti-digoxin containing reaction tube.

The tube is rocked at RT for 2h or overnight at 4 C. Unreacted sites on the Sepharose are blocked by adding bovine serum albumin at a concentration of 5 mg/ml BSA. The mixture is incubated for 2h at RT. The Sepharose is pelleted, the supernatant removed, and the pellets dispersed in 0.2M glycine, pH 8.0, followed by rocking for 2h at RT or overnight at 4 C. Excess absorbed protein is removed by placing the Sepharose on a sintered glass funnel, followed by washing with several volumes of acetate buffer (0.1M sodium acetate, 0.5M NaCl, pH 4.0), followed by several volumes of the coupling buffer, alternating buffer washes. The resulting particles are then suspended in assay buffer, containing 5 mg/ml BSA and 0.1% sodium azide and stored at 4 C.

Assay buffer is prepared by combining 2.5 g monobasic potassium phosphate, 23 g dibasic potassium phosphate, 1.7 g sodium monobasic phosphate, monohydrate, 12.5 g sodium dibasic phosphate, 0.644 g magnesium acetate tetrahydrate, 1.3 g sodium azide, 12.25 ml ethylene glycol, and 100 ml of 10X EGTA solution (7.6 g EGTA, 1.6 g sodium hydroxide in 200 ml water) and 5 ml 10% Tween 20 in 10 mM dithiothreitol and the solution brought to 1 liter. (EGTA is ethylene-bisoxyethylenenitrilo tetraacetic acid.)

The following table indicates the amount of materials used in the above procedure.

TABLE 1

| Lot # | Activated Sepharose g | Coupled Anti-digoxin mg | Coupling Solution ml | Added BSA** mg |
|---|---|---|---|---|
| I | 1 | 15.8 | 5 | 0 |
| II | 2 | 7.77 | 12 | 95 |
| III | 2 | 2.1* | 10 | 30 |
| IV | 2 | 0.63* | 10 | 50 |

*BSA (bovine serum albumin) was added to the coupling solution to a total protein concentration of 2 mg/ml.
**BSA added at 2h.

To perform the assay, various concentrations of digoxin, ranging from 5 ng/ml to 0.025 ng/ml, were preincubated with either anti-digoxin Sepharose or BSA-Sepharose as a control. A fixed concentration of ED-digoxin conjugate was added to the digoxin/anti-digoxin Sepharose tests and incubated. In some instances, goat anti-rabbit immunoglobulin (GARS) was added to determine the effect of anti-antibody.

The specific procedure is as follows. Antidigoxin Sepharose Lot IV in assay buffer containing 5 mg/ml BSA was prepared as a 50% slurry, and then 35 μl of slurry was mixed with 165 μl of carrier sepharose and transferred to a 1.5 ml microfuge tube. To the tube was then added 100 μl of digoxin at the desired concentration and the tube rocked at RT for 30 min. To the tube was then added 100 μl of enzyme donor (ED-4)-digoxin (see application Ser. No. 721,267 now U.S. Pat. No. 4,708,929) to provide a final concentration of $8 \times 10^{-10}$M. At this point GARS was added, as appropriate to provide a final dilution in the tube of 1:750. The tests were then developed with 100 μl developer ($2.5 \times 10^{-6}$ M enzyme acceptor, and 3.05 mg/ml o-chlorophenol red-$\beta$-galactoside (CPRG) to provide a final concentration of enzyme acceptor $5.0 \times 10^{-7}$M and CPRG of 0.61 mg/ml. After rocking each tube for 22 min at RT, the reaction was stopped by adding 100 μl of isopropylthiogalactoside (240 mM) (IPTG) to provide a final concentration of 40 mM. The Sepharose was then pelleted in the microfuge and 100 μl of supernate was transferred to a microtiter well and the absorbance read at 577 nm in a Titertek spectrophotometer. Alternatively, the absorbance could be measured through the tube without any separation using an appropriate spectrophotometer.

The following table indicates the results.

TABLE 2

| Digoxin ng/ml | OD at 577 nM | |
|---|---|---|
| | −GARS | +GARS |
| 5 | 784 | 839 |
| 0.5 | 684 | 732 |
| 0.25 | 561 | 542 |
| 0.2 | 490 | 507 |
| 0.1 | 351 | 338 |
| 0.05 | 324 | 328 |
| 0.025 | 268 | 286 |
| 0.0 no Sepharose | 839 | |

The above results demonstrate one can modulate the enzyme activity over a digoxin concentration range of 0 to 5 ng/ml, being able to detect as little as 0.025 ng/ml of digoxin. Furthermore, the presence of antibody to the anti-digoxin does not appear to have any significant effect on the enzyme activity. The background signal can be reduced by varying a number of factors either individually or simultaneously, viz. lower EA concentration, varying development time and using more pure enzyme donor mip conjugates.

EXAMPLE 2

Materials and Methods

Materials

For the production of ED-fab conjugates all (ascities) antibodies were obtained from Beckman Instruments Inc., Irvine, Calif. Enzyme Acceptor (EA) and lyophilized Enzyme Donor (ED) were obtained from Microgenics Inc., Concord, Calif. Carboxyl-modified polystyrene microparticles were obtained from Polysciences Inc., Warrington, Pa. and from Polymer Laboratories, UK. The hCG used in the preparation of latex conjugates was from Sigma, St. Louis, Mo. hCG from Scripps, San Diego, Calif. was used in the sample calibrators. Pooled, delipidated whole human serum was obtained from Biocell, Carson, Calif. CPRG from Peninsula Labs, Burlingame, Calif. was used as a substrate.

Enzyme Donor-fab Fragment Conjugate Preparation

Antibody selection, characterization, digestion and purification. Anti-hCG monoclonal antibodies were screened for crossreactivity to LH and TSH by immunoblotting techniques. Affinity was evaluated by Scatchard analysis. Selected antibodies were purified on a $90 \times 2.5$ cm hydroxylapatite (Calbiochem) column using a linear gradient elution of 20 to 300 mM KP04 pH 6.8. Each purified antibody was then characterized for optimal Fab yield when digested with mercuripapain (Sigma). Digests were purified on a $10 \times 2.5$ cm DEAE column (high-capacity ion-exchange cellulose, Pierce), equilibrated with TRIS-HCl pH8 and eluted with a 0 to 300 mM NaCl gradient. Fractions were analysed by immunoelectrophoresis and those containing pure Fab were pooled, concentrated using PEG, and dialyzed in 100 mM sodium phosphate, 4 mM EDTA, pH 7.4

ED iodination and purification. Production-grade ED4 (see U.S. Pat. No. 4,708,929) was mixed with radiolabeled ED4-TNB (carried out by standard methods) and purified using reverse-phase HPLC chromatography. The ED was pooled and the concentration and radioconjugatability determined. Aliquots were lyophilized and stored at −20° C.

Conjugation: covalent heterobifunctional coupling through sulfosuccinimidylmaleimidomethylcyclohexane-1-carboxylate (SMCC). Each conjugate was prepared as follows: One mg of pure Fab was activated for 15 min at room temperature with 2 mM sulfo-SMCC (Pierce Chemical Co.) in 10 mM sodium phosphate, 150 mM NaCl (PBS), pH 7.3. The activated Fab was separated from the excess SMCC on a Sephadex G-25 PD-10 column (Pharmacia) equilibrated in degassed PBS. The results of back titrations showed there to be approximately 2 to 3 maleimides per Fab following activation. To ensure that there is adequate excess ED in the conjugation reaction, a ratio of 3 moles ED to 1 maleimide is used. ONce the amount of ED required is determined, the lyophilized ED is reconstituted with the activated Fab and allowed to react for 1 hr at room temperature. The concentration of the crude conjugate is determined by OD 280 and by counts/min data. To remove the excess ED, the conjugate is purified using a Superose 12 (Pharmacia) column on a FPLC. Pooled fractions containing the final product were aliquoted and stored at −20° C.

Preparation of hCG-Latex Conjugates

Covalent coupling of hCG to carboxlylated polystyrene microparticles by the "carbodiimide" method. The protocol used is an adaptation of one published by Polysciences. The hCG-latex conjugates are prepared as follows: 2 ml of a 10% solids stock suspension of 70 nm polystyrene particles (Polysciences) are washed using an Amicon Ym100 filter apparatus with 100 ml of 100 mM carbonate buffer, pH 9.6. The Amicon wash is repeated, this time using 100 ml of a 20 mM sodium phosphate buffer, pH 4.5. The latex is resuspended in 5 ml of the phosphate buffer and 10 ml of a fresh 2% 1-(3-dimethylaminopropyl)-3-ethyl carbodiimide hydrochloride (EDAC) phosphate buffer solution is added dropwise. The reaction mixture is agitated for 15 min at room temperature on a rocker table. Following this (EDAC) activation step the 70 nm latex is pelleted in a microfuge. The mixture is divided into Eppendorf centrifuge tubes, spun for 10 min and the supernatant discarded. To remove the unreacted carbodiimide, the pellets are resuspended in 200 mM borate buffer, pH 8.5 and washed three times in the same manner. The pellets are then resuspended and pooled in 20 ml of in borate buffer. The coupling protein, hCG, is added at approximately 3 mg/ml latex and the reaction is mixed overnight on a rocker at −5° C. Next, 800 μl of 250 mM ethanolamine in borate buffer is added to block unreacted sites on the microparticles. After a 30 minute incubation on a rocker at room temperature, the latex is pelleted in a microfuge. The supernatant is saved for protein determination. To block any remaining non-specific protein binding sites the latex is suspended in borate buffer containing 10mg/ml of L-α-aspartyl-L-phenylalanine methyl ester (APM) and PVP-40 at 1 mg/ml. The reaction is allowed to continue for 4 more hrs at room temperature. The latex is then washed extensively using the Amicon Ym100 filter with PBS, pH 7.4 (approximately 200 ml). The final preparation is resuspended in 2 ml PBS containing 10 mg/ml BSA, 5% glycerol and 0.1% sodium azide (storage buffer).

Prior to use in the Cobas Bio assay, the latex is washed using the Amicon filter apparatus with approximately 200 ml of the assay buffer: 200 mM potassium phosphate, 100 mM sodium phosphate, 3 mM magnesium acetate, 20 mM sodium azide, 50 mM ethylene glycol, 160 mM EGTA, 0.01% Tween-20, pH 7.0.

Cobas Bio Application for a Homogeneous hCG Immunoassay Using a Latex Inhibitor

Assay protocol.

a. Preincubation. Patient samples are incubated with ED-Fab conjugate for 5 min at 37° C.

b. Cobas Bioassay.

(1) 50 μl preincubated sample is mixed with 150 μl hCG-latex reagent for 5 min.

(2) 30 μl start reagent ($5.0 \times 10^{-7}$M EA 22; 0.61 mg/ml CPRG) is added and 30-sec readings at OD 574 are taken.

c. Interpretation. Complementation activity is a function of increasing serum hCG levels. As hCG increased, more ED-Fab binds analyte to hCG in the preincubation step. This leaves less ED-Fab available for inhibition binding by hCG-latex.

The following table indicates the results:

TABLE 3

| MIu/ml | M [sample] | M [system] | $OD_{574}$ (mAU/min) |
|---|---|---|---|
| ~37 | $1 \times 10^{-10}$ | $1 \times 10^{-11}$ | 209 |
| ~185 | $5 \times 10^{-10}$ | $1 \times 10^{-11}$ | 220 |
| ~370 | $1 \times 10^{-9}$ | $1 \times 10^{-10}$ | 234 |
| ~1850 | $5 \times 10^{-9}$ | $1 \times 10^{-10}$ | |
| ~3700 | $1 \times 10^{-8}$ | $1 \times 10^{-9}$ | 294 |
| ~18,500 | $5 \times 10^{-8}$ | $1 \times 10^{-9}$ | |
| ~37,000 | $1 \times 10^{-7}$ | $1 \times 10^{-8}$ | 307 |

It is evident from the above results, that an effective sensitive assay is provided which allows for the detection of a variety of analytes at low concentrations. The assay can be performed over relatively short periods of time in a simple protocol without a separation step or washing, so as to minimize errors introduced by handling and variable processing. In this manner, accurate results are obtained in a reproducible manner, where a wide variety of spectrophotometers or fluorimeters may be employed as if the assay was in fact homogeneous.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining the presence of an analyte in a sample, said analyte being a member of a specific binding pair ("mip"), said method employing as reagents fragments of beta-galactosidase comprising an N-terminal enzyme donor fragment ("ED") and a C-terminal enzyme acceptor fragment ("EA"), where said acceptor and donor fragments when joined together form an active enzyme complex and said enzyme donor is conjugated to a mip to form a mip/ED conjugate which is immunologically competitive with or complementary to said analyte; and wherein a mip, complementary to said mip/ED conjugate and/or said analyte, is attached to a macromolecule of at least about 250 kda or attached to a solid surface to form immobilized mip:

said method comprising:

contacting in an assay medium, said sample, said mip/ED conjugate, said EA, said immobilized mip, and enzyme substrate, wherein said immobilized mip and said mip/ED conjugate are complementary and mip/ED conjugate bound to said immobilized mip is substantially inhibited in forming an enzymatically active complex; and determining the enzyme activity of said assay medium in comparison to an assay medium having a known amount of analyte.

2. A method according to claim 1, wherein said contacting comprises combining said sample, said mip/ED conjugate and said immobilized and incubating prior to addition of said enzyme acceptor and said substrate, wherein said immobilized mip is complementary to said analyte.

3. A method according to claim 1, wherein said contacting comprises combining said sample and said immobilized mip and incubating in a first step; adding said mip/ED conjugate and incubating in a second step; and adding said EA and said substrate in a third step.

4. A method according to claim 1, wherein said contacting comprises combining said sample and said mip/ED conjugate in a first step, wherein said analyte and mip/ED conjugate are complementary and said mip/ED conjugate is monovalent in relation to said immobilized mip and in substantial binding excess to said analyte, and incubating for a time sufficient for complex formation to occur; adding immobilized mip in substantial binding excess to said mip/ED conjugate and incubating for sufficient time for complex formation to occur; and adding EA and substrate.

5. A method according to claim 4, wherein said mip/ED conjugate comprises a Fab fragment specific for said analyte.

6. A method according to claim 4, wherein said immobilized mip is mip bound to particles of from about 20 to 200 nm.

7. A method according to claim 1, wherein said analyte is an antigen.

8. A method according to claim 7, wherein said antigen is a protein.

9. A method according to claim 1, wherein said analyte is a hapten.

10. A method for determining the presence of an analyte in a sample, said analyte being a member of a specific binding pair ("mip"), said method employing as reagents fragments of beta-galactosidase comprising an N-terminal enzyme donor fragment ("ED") and a C-terminal enzyme acceptor fragment ("EA"), where said acceptor and donor fragments when joined together form an active enzyme complex and said enzyme donor is conjugated to a mip to form a mip/ED-conjugate which is immunologically competitive with said analyte; and wherein a mip, complementary to said mip/ED conjugate and said analyte, is immobilized;

said method comprising:

contacting in an assay medium, said sample, said mip/ED conjugate, and immobilized mip and incubating for sufficient time for complex formation to go to substantial completion to provide a first mixture, wherein said mip/ED conjugate bound to said immobilized mip is substantially inhibited in forming an enzymatically active complex;

adding said EA, substrate and any additional reagents necessary to produce a detectable product; and determining the enzyme activity of said assay medium by means of said detectable product in comparison to an assay medium, having a known amount of analyte.

11. A method according to claim 10, wherein said immobilized mip is an antibody.

12. A method according to claim 10, wherein said immobilized mip is bound to a microtiter plate well.

13. A method for determining the presence of an analyte in a sample, said analyte being a member of a specific binding pair ("mip"), said method employing an N-terminal enzyme donor fragment ("ED") and a C-terminal enzyme acceptor fragment ("EA"), where said acceptor and donor fragments when joined together, form an active enzyme complex and said enzyme donor is conjugated to a mip to form a mip/ED conjugate which is complementary to said analyte; and wherein a mip complementary to said mip/ED conjugate is immobilized;

said method comprising:

contacting in an assay medium, said sample and said mip/ED conjugate in substantial binding excess to said analyte, and incubating for a sufficient time for complex formation to go to substantial completion to form a first assay medium;

combining said first assay medium, with said immobilized mip, said immobilized mip being in substantial binding excess to said mip/ED conjugate to form a second assay medium, wherein said mip/ED conjugate bound to said immobilized mip is substantially inhibited in forming an enzymatically active complex;

combining, either concurrently or consecutively with said immobilized mip, EA, substrate and any additional reagents necessary to produce a detectable product; and determining the enzyme activity of said second assay medium by means of said detectable product in comparison to an assay medium having a known amount of analyte.

14. A method according to claim 13, wherein said EA is added consecutively and said second assay medium is incubated prior to EA addition.

15. A method according to claim 13, wherein said determining is by means of an automated device.

16. A method according to claim 13, wherein said analyte is a ligand, said immobilized mip is ligand or cross-reactive analog thereof, and said mip/ED conjugate comprises a Fab fragment specific for said analyte.

17. A method according to claim 16, wherein said ligand is a protein.

18. A method according to claim 16, wherein said ligand is a hapten.

19. A method according to claim 13, wherein said immobilized mip is bound to particles of from about 20 to 200 nm.

20. The method according to any one of claims 1, 10 or 13 wherein said determining is in the absence of a separation step.

* * * * *